(12) United States Patent
Ormsby

(10) Patent No.: US 8,734,419 B2
(45) Date of Patent: May 27, 2014

(54) CLOTH TRAINING DIAPER

(75) Inventor: Kim Ormsby, Bozeman, MT (US)

(73) Assignee: The Natural Baby Company, LLC, Bozeman, MT (US)

( * ) Notice: Subject to any disclaimer, the term of this patent is extended or adjusted under 35 U.S.C. 154(b) by 134 days.

(21) Appl. No.: 13/620,429

(22) Filed: Sep. 14, 2012

(65) Prior Publication Data

US 2014/0081232 A1    Mar. 20, 2014

(51) Int. Cl.
*A61F 13/15*    (2006.01)

(52) U.S. Cl.
USPC ........... 604/399; 604/396; 604/394; 604/387; 604/385.15

(58) Field of Classification Search
USPC ..................... 604/399, 396, 394, 387, 385.15
See application file for complete search history.

(56) References Cited

U.S. PATENT DOCUMENTS

| | | | |
|---|---|---|---|
| 2,016,356 A | 10/1935 | Alsop | |
| 2,493,492 A | 1/1950 | Malamut | |
| 4,315,508 A | 2/1982 | Bolick | |
| 4,555,244 A | 11/1985 | Buell | |
| 4,834,736 A | 5/1989 | Boland et al. | |
| 4,834,738 A | 5/1989 | Kielpikowski et al. | |
| 4,834,742 A | 5/1989 | Wilson et al. | |
| 4,846,825 A | 7/1989 | Enloe et al. | |
| 4,872,871 A | 10/1989 | Proxmire et al. | |
| 4,895,569 A | 1/1990 | Wilson et al. | |
| 5,304,162 A | 4/1994 | Kuen | |
| 5,374,262 A | 12/1994 | Keuhn, Jr. et al. | |
| 5,386,595 A | 2/1995 | Kuen et al. | |
| 5,620,431 A | 4/1997 | LeMahieu et al. | |
| 5,649,914 A | 7/1997 | Glaug et al. | |
| 5,669,901 A | 9/1997 | LaFortune et al. | |
| 5,702,376 A | 12/1997 | Glaug et al. | |
| 5,797,892 A | 8/1998 | Glaug et al. | |
| 6,313,372 B1 | 11/2001 | Suzuki | |
| 6,627,786 B2 | 9/2003 | Roe et al. | |
| 6,676,648 B2 | 1/2004 | Bruemmer Prestley et al. | |
| 6,895,603 B2 | 5/2005 | Coates | |
| 6,972,012 B1 | 12/2005 | Posniak et al. | |
| 7,629,501 B2 | 12/2009 | Labit et al. | |
| 7,704,589 B2 | 4/2010 | Olson et al. | |
| 7,767,876 B2 | 8/2010 | Davis et al. | |
| 7,781,640 B2 | 8/2010 | Davis et al. | |
| 7,914,507 B1 | 3/2011 | Magee | |
| 7,915,476 B2 | 3/2011 | Long et al. | |
| 7,977,528 B2 | 7/2011 | Vargo et al. | |
| 2001/0031957 A1 | 10/2001 | Prestley et al. | |
| 2002/0010452 A1 | 1/2002 | Dupuy | |
| 2003/0100872 A1 | 5/2003 | Roe et al. | |
| 2003/0120253 A1 | 6/2003 | Wentzel et al. | |
| 2003/0199845 A1 | 10/2003 | Roe et al. | |
| 2003/0216705 A1 | 11/2003 | Coates | |
| 2004/0254549 A1 | 12/2004 | Olson et al. | |
| 2005/0096612 A1 | 5/2005 | Davis et al. | |

(Continued)

*Primary Examiner* — Jacqueline F. Stephens
(74) *Attorney, Agent, or Firm* — Antoinette M. Tease

(57) ABSTRACT

A cloth training diaper comprising an outer layer coupled to an inner layer, a front portion and a rear portion, a plurality of snaps arranged longitudinally along the right side of the front portion, the left side of the front portion, the right side of the rear portion, and the left side of the rear portion, the snaps extending through the outer and inner layers, and two side panels, each side panel comprised of a smocked material coupled to a non-smocked material, each side panel having a right side and a left side and a plurality of snaps arranged along the right and left sides of the smocked material. The snaps on the side panels engage with the snaps on the front and rear portions.

5 Claims, 5 Drawing Sheets

(56) References Cited

U.S. PATENT DOCUMENTS

| | | |
|---|---|---|
| 2005/0222546 A1 | 10/2005 | Vargo et al. |
| 2006/0068168 A1 | 3/2006 | Olson et al. |
| 2006/0069364 A1 | 3/2006 | Davis et al. |
| 2006/0142729 A1 | 6/2006 | Sivilich et al. |
| 2006/0224132 A1 | 10/2006 | Roe et al. |
| 2007/0049884 A1 | 3/2007 | Long et al. |
| 2007/0191797 A1 | 8/2007 | Roe et al. |
| 2007/0233028 A1 | 10/2007 | Roe et al. |
| 2008/0065034 A1 | 3/2008 | Vargo et al. |
| 2008/0065039 A1 | 3/2008 | Labit et al. |
| 2009/0204088 A1 | 8/2009 | Stearman et al. |
| 2009/0306613 A1 | 12/2009 | Roe et al. |
| 2010/0087794 A1 | 4/2010 | Labit et al. |
| 2010/0130955 A1 | 5/2010 | Tice |
| 2010/0168709 A1 | 7/2010 | Hodgkin |
| 2011/0144602 A1 | 6/2011 | Long et al. |

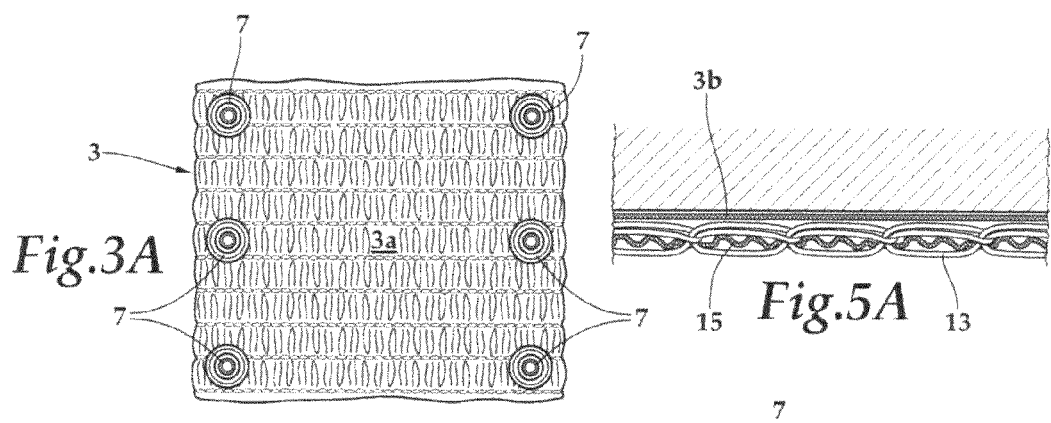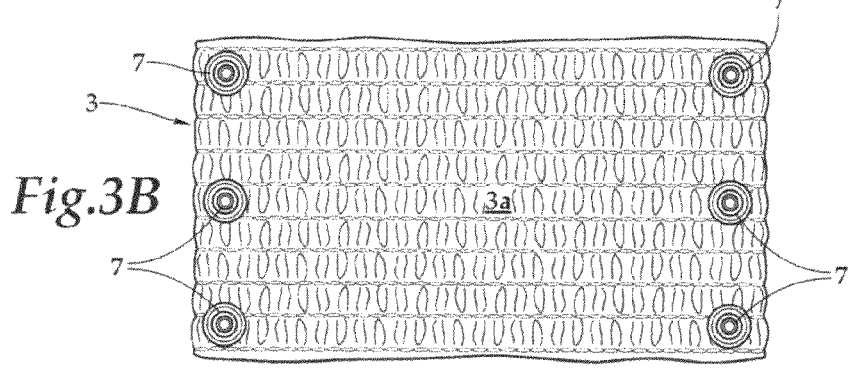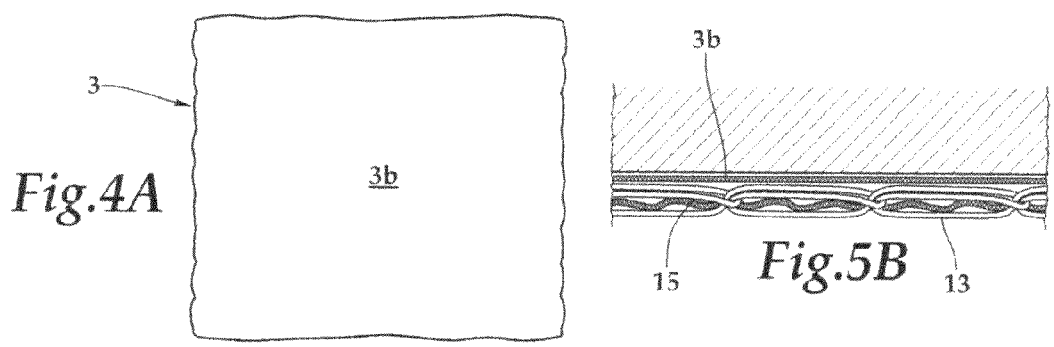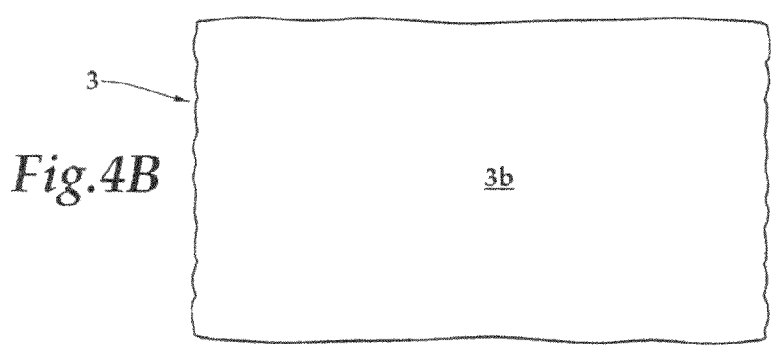

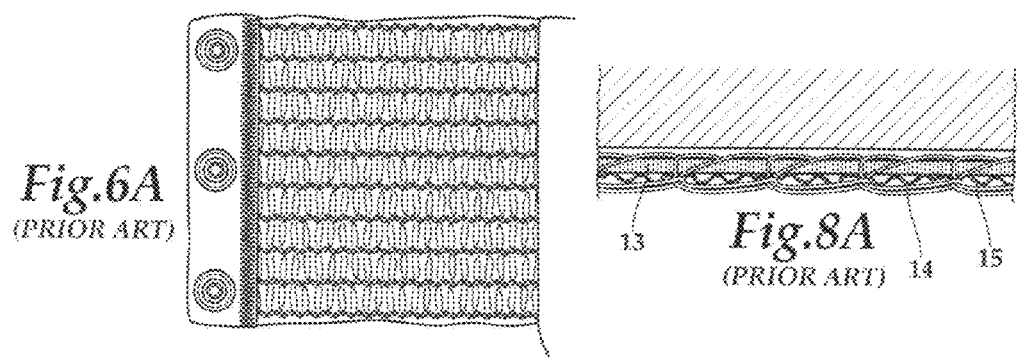
Fig.6A (PRIOR ART)
Fig.8A (PRIOR ART)
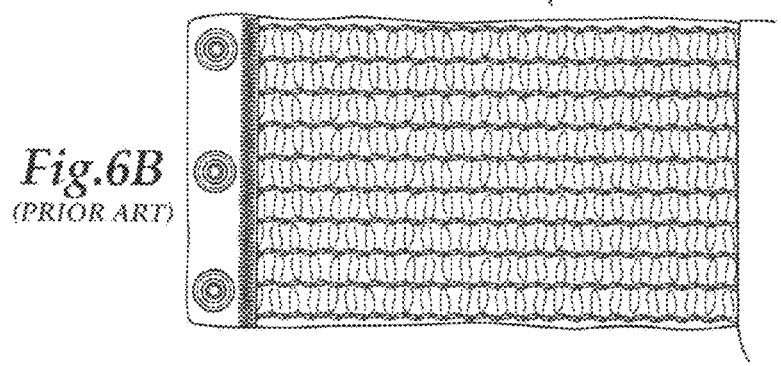
Fig.6B (PRIOR ART)
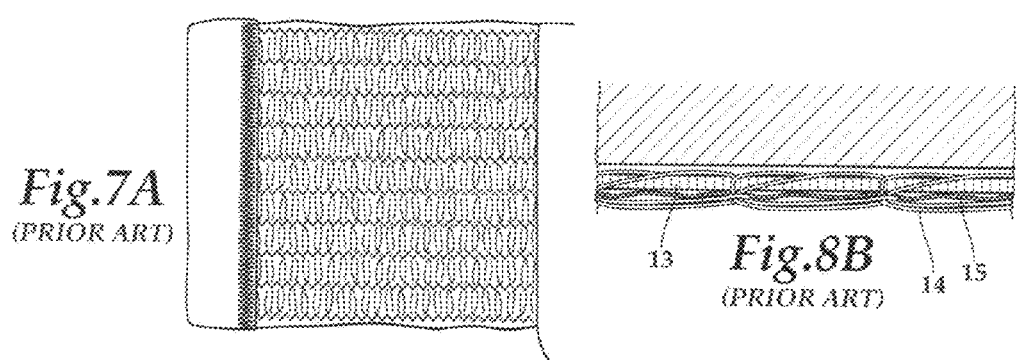
Fig.7A (PRIOR ART)
Fig.8B (PRIOR ART)
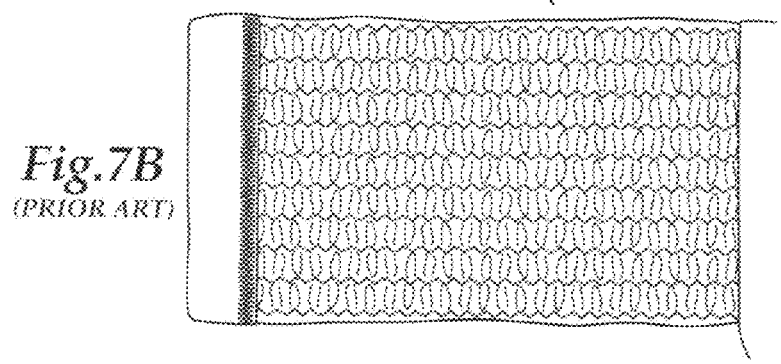
Fig.7B (PRIOR ART)

CLOTH TRAINING DIAPER

BACKGROUND OF THE INVENTION

1. Field of the Invention

The present invention relates generally to the field of cloth diapers, and more generally, to a cloth training diaper with removable side panels, an inner pocket, and uniquely flexible side panels.

2. Description of the Related Art

The present invention is designed to provide a "training underwear" option that has adjustable size (due to the removable, elasticized side panels and rise snaps) to allow it to fit a myriad of body shapes and sizes, adjustable absorbency (due to the longitudinal pocket for inserting additional absorbent material), and adjustable style (interchangeable side panels come in different colors, which allows the customer to mix and match colors). The present invention is a pull-on style training pant with a waterproof outer and hidden absorbent layer that forms the back of the pocket. The inner pocket allows the customer to add absorbent material to the trainer to increase its absorbency for naps and nighttime. The side panels may be completely removed and replaced with larger versions of the side panels as the child grows, thereby increasing the size of both the waist and leg openings.

the prior art includes a number of cloth diapers and/or training pants, but none of these other inventions offers: completely removable, snap-on side panels; a longitudinal inner pocket for additional absorbency that extends the entire length of the trainer; and flexible (smocked) side panels that provide elasticity but also present a smooth, non-smocked surface against the child's skin. Although smocking has been done for centuries in connection with garments, the smocking technique of the present invention is unique. Rather than attaching an elastic thread to one side of the material by weaving non-elastic thread around the elastic thread and through the material, as is done in the prior art, the smocking of the present invention is created by actually weaving the elastic thread through the smocking material, as is shown in detail in connection with the figures.

U.S. Patent Application Pub. No. 2010/0130955 (Tice) discloses a diaper with smocked side panels, but these side panels are created using the prior art smocking technique described above. In addition, the side panels do not include a smooth, non-smocked material on the inner side of the side panel to prevent the smocking material from creating friction against the wearer's skin. Furthermore, this diaper does not include a pocket, and the side panels are not completely removable.

U.S. Pat. No. 7,629,501 (Labit et al., 2009) provides a reusable diaper with an inner pocket, but the side panels are not removable, and there is no smocking. Also, there is a flap that conceals the slot that forms the entry into the pocket to prevent access to the pocket when not desired, whereas the present invention is intentionally designed to allow the pocket to be readily accessible at all times.

U.S. Pat. No. 7,704,589 (Olson et al., 2010) describes a diaper with stretchable side panels, but these panels are not removable, nor are they formed with the unique smocking stitch of the present invention. In addition, this diaper does not include an inner pocket. U.S. Patent Application Pub. Nos. 2006/0142729 (Sivilich et al.) and 2003/0120253 (Wentzel et al.) both show diapers with removable strips or fasteners on either side of the diaper. These strips or fasteners are not smocked, and the diapers do not include inner pockets.

BRIEF SUMMARY OF THE INVENTION

The present invention is a cloth training diaper comprising: an outer layer coupled to an inner layer; a front portion and a rear portion; a plurality of snaps arranged longitudinally along the right side of the front portion, the left side of the front portion, the right side of the rear portion, and the left side of the rear portion, the snaps extending through the outer and inner layers; and two side panels, each side panel comprised of a smocked material coupled to a non-smocked material, each side panel having a right side and a left side and a plurality of snaps arranged along the right and left sides of the smocked material, wherein the snaps on the side panels engage with the snaps on the front and rear portions.

In a preferred embodiment, the smocked material of the side panels is formed by weaving elastic thread through a layer of fabric. Preferably, the invention further comprises a pocket that is disposed between the inner and outer layers and that extends longitudinally from a top of the front portion to a top of the rear portion and that is as wide as the front and rear portions.

In a preferred embodiment, the front portion and the rear portion each comprises an elasticized top, wherein the inner layer is comprised of a first piece of material and a second piece of material, wherein the first piece of material forms a downwardly extending flap proximate the elasticized top of the rear portion, and wherein the second piece of material forms an upwardly extending flap that lies on top of the downwardly extending flap to form an opening for the pocket. Preferably, the invention further comprises two pairs of rise snaps on the front portion on the outer layer.

BRIEF DESCRIPTION OF THE DRAWINGS

FIG. 3A is a plan view of a fast side of the side panel of the present invention shown in a relaxed state.

FIG. 3B is a plan view of a first side of the side panel of the present invention shown in an extended state.

FIG. 4A is a plan view of a second side of the side panel of the present invention shown in a relaxed state.

FIG. 4B is a plan view of a second side of the side panel of the present invention shown in an extended state.

FIG. 5A is a section view of the side panel of the present invention shown in a relaxed state.

FIG. 5B is a section view of the side panel of the present invention shown in an extended state.

FIG. 6A is a plan view of a first side of the side panel of a prior art cloth diaper shown in a relaxed state.

FIG. 6B is a plan view of a first side of the side panel of a prior art cloth diaper shown in an extended state.

FIG. 7A is a plan view of a second side of the side panel of a prior art cloth diaper shown in a relaxed state.

FIG. 7B is a plan view of a second side of the side panel of a prior art cloth diaper shown in an extended state.

FIG. 8A is a section view of the side panel of a prior art cloth diaper shown in a relaxed state.

FIG. 8B is a section view of the side panel of a prior art cloth diaper shown in an extended state.

FIG. 9 is a second perspective view of the present invention shown from the inside of the diaper.

FIG. 10 is a third perspective view of the present invention showing the insertion of absorbent material into the longitudinal pocket.

FIG. 11 is a fourth perspective view of the present invention showing the absorbent material completely inserted into the longitudinal pocket.

REFERENCE NUMBERS

Figure 1:
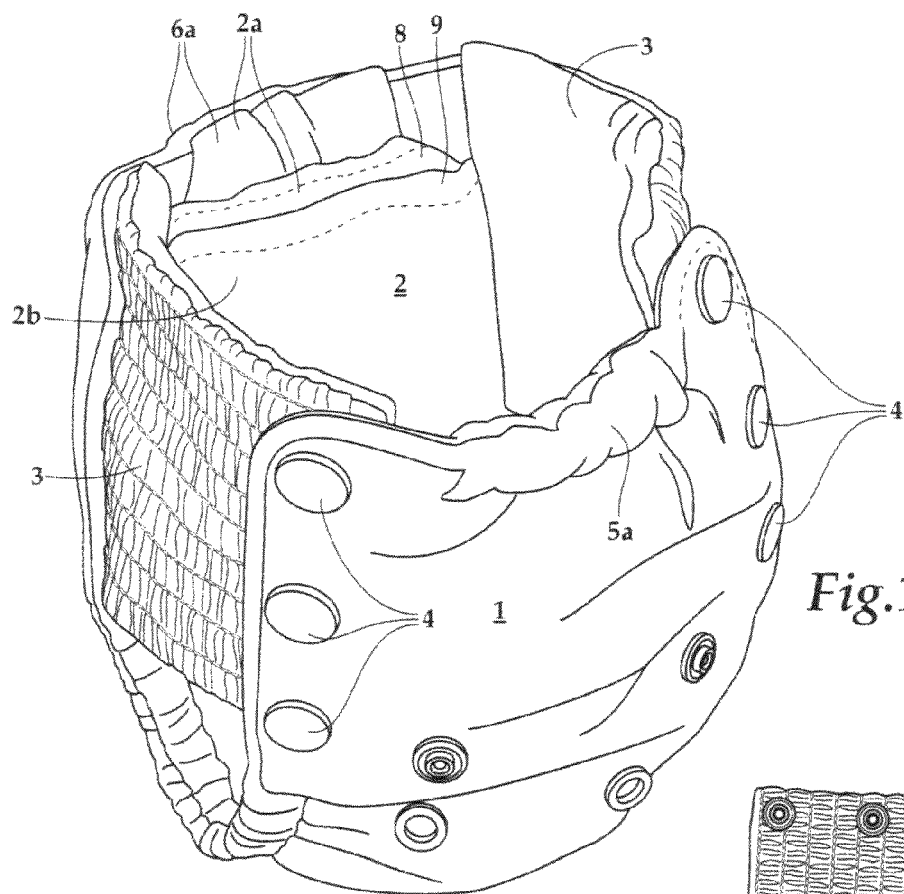
FIG. 1 is a first perspective view of the cloth training diaper of the present invention.

1 Outer layer
2 Inner layer
2a First piece of material (forming inner layer)
2b Second piece of material (forming inner layer)
3 Side panel
3a Smocked side/material (of side panel)
3b Non-smocked side/material (of side panel)
4 Snap
5 Front portion
5a Top (of front portion)
6 Rear portion
6a Top (of rear portion)
7 Leg area
8 Downwardly extending flap
8a Bottom edge (of downwardly extending flap)
9 Upwardly extending flap
10 Pocket
11 Super-absorbent material
12 Additional absorbent material
13 Elastic thread
14 Non-elastic thread
15 Smocked material (in prior art example)

DETAILED DESCRIPTION OF INVENTION

FIG. 1 is a first perspective view of the cloth training diaper of the present invention. As shown in this figure, the invention comprises an outer layer 1, an inner layer 2, and two side panels 3. The side panels 3 are each smocked (the smocking is described more fully below), and they are both flexible and elastic (i.e., they can stretch to accommodate a child's growth in the waist and/or leg area). In addition, as shown more fully in connection with FIG. 2, each side panel 3 attaches to a series of three longitudinally aligned snaps 4 located on either side (right and left) of the front portion 5 and either side (right and left) of the rear portion 6 of the invention. The snaps 4 extend through both the outer and inner layers 1, 2, and the side panels 3 preferably attach as the snaps 4 on the inside of the diaper; however, the side panels 3 could also attach to the snaps 4 on the outside of the diaper.

Figure 2:
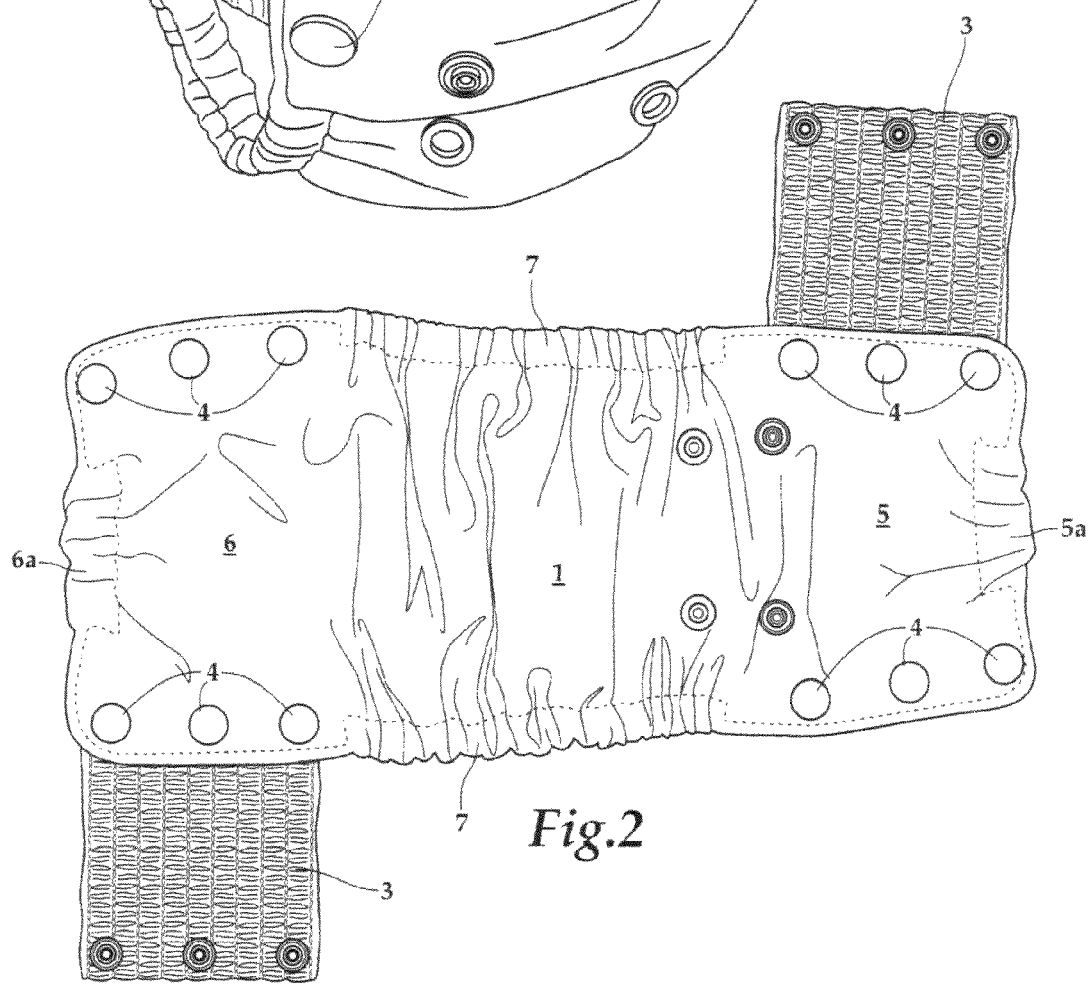
FIG. 2 is a plan view of the cloth training diaper of the present invention.

FIG. 2 is a plan view of the cloth training diaper of the present invention. As shown in this figure, each side panel 3 is completely removable. To remove the side panel 3, one would simply unsnap it from the front and rear portions 5, 6 of the diaper. To the best of the inventors knowledge, no prior art diaper or training pant provides completely removable, smocked side panels.

Note that the outer and inner layers 1, 2 are preferably elasticized in the leg areas 7 an also at the top 5a, 6a of the irons and rear portions 5, 6. The inner layer is preferably comprised of two pieces of material. The first piece of material 2a forms the top 6a of the rear portion 6 (on the inside of the diaper only), and it also forms a downwardly extending flap 8 located directly beneath the top 6a of the rear portion 6. This downwardly extending flap 8 extends from one side of the inner layer 2 to the other. The second piece of material 2b that forms the inner layer 2 extends from the top 5a of the front portion 5 to the downwardly extending flap 8 (but does not include the downwardly extending flap 8). The end of the second piece of material 2b opposite that of the top 5a (i.e., the end proximate the top 6a of the rear portion 6) forms an upwardly extending flap 9 that lies already over the bottom edge 8a of the downwardly extending flap 8. The upwardly extending flap 9 is attached (sewn) to the downwardly extending flap on either side of the upwardly extending flap 9. The downwardly extending flap 8 and upwardly extending flap 9 together form an opening for the pocket 10 (see FIGS. 9-11). Because the upwardly extending flap 9 lies on top of the downwardly extending flap 8 (and not the other way around), the pocket is always easily accessible and never closed.

Between the outer 1 and inner 2 layers is a super-absorbent layer of material 11 (see FIG. 9). In a preferred embodiment, this material is comprised of hemp or cotton. The super-absorbent material 11 extends the entire length and width of the diaper, from the top 5a of the front portion 5 to the top 6a of the rear portion, as does the pocket 10. (Although the additional absorbent material 12 shown in FIGS. 10 and 11 does not extend the entire length or width of the diaper, the pocket 10 actually does.) Additional absorbent material 12 may be inserted into the pocket 10 (see FIGS. 10-11) and is easily removed.

FIG. 3A is a plan view of a first side of the side panel of the present invention sheen in a relaxed state. As shown in this figure, each side of the side panel 3 comprises three snaps 7 corresponding to the snaps 7 on the front and rear portions 5, 6 of the diaper. Thus, the side panels 3 are completely removable and interchangeable. As noted above, larger (longer) side panels may be used to accommodate growth of the child.

FIG. 3B is a plan view of a first side of the side panel of the present invention shown in an extended state. Because of the elastic stitching that is literally woven into the first side of each side panel 3 (see FIG. 5A), the side panels can stretch and compress.

FIG. 4A is a plan view of a second side of the side panel of the present invention shown in a relaxed state. In a preferred embodiment, the first side 3a of each side panel 3 (i.e., the smocked side shown in FIGS. 3A and 3B) faces outward (away from the child's skin) and is attached (sewn) around its perimeter to a non-smocked material 3b that is smooth and flat (not smocked). The smooth, flat side 3b of each side panel (i.e., the side shown in FIGS. 4A and 4B) is the side that lies against the child's skin. This coupling of a smocked material 3a with a non-smocked material 3b makes the side panels 3 much more comfortable against the child's skin and further differentiates the present invention from prior art.

FIG. 4B is a plan view of a second side of the side panel of the present invention shown in an extended state. The non-smocked material 3b is preferably elastic so that it can stretch and compress with the smocked side 3a of the side panel 3.

FIG. 5A is a section view of the side panel of the present invention shown in a relaxed state, and FIG. 5B is a section view of the side panel of the present invention shown in an extended state. As shown in both of these figures, the elastic thread 13 is literally woven through the fabric 15 to create the smocking.

FIG. 6A is a plan view of a first side of the side panel of a prior art cloth diaper shown in a relaxed state, and FIG. 6B is a plan view of a first side of the side panel of a prior art cloth diaper shown in an extended state. FIG. 7A is a plan view of a second side of the side panel of a prior art cloth diaper shown in a relaxed state, and FIG. 7B is a plan view of a second side of the side panel of a prior art cloth diaper shown in an extended state. These figures are specifically in reference to the invention described and shown in U.S. Patent Application Pub. No. 2010/0130955 (Tice). In the later invention, the side panels comprise a single layer of smocked material, which rubs and chafes against the child's skin.

In addition, the smocking is not accomplished in the same way as in the present invention. Rather than actually weaving the elastic thread 13 into the smocked material (see FIGS. 5A and 5B), the elastic thread 13 is positioned on one side of the material only and is attached to the material 15 with a non-elastic thread 14 that wraps around the elastic thread 13 and is woven through the material—in this case, with an "x" stitch on one side (over the elastic thread 13) and a loop stitch on the other. In this figure, the surface of the side panel with the relatively thick, elastic thread 13 on it (i.e., the top side of FIG. 8A) is in direct contact with the child as skin.

FIGS. 9, 10 and 11 illustrate the insertion of additional material 12 into the pocket 10, which extends longitudinally from the top 5a of the front portion 5 to the top 6a of the rear portion 6a. As noted above, the present invention is designed so that the pocket opening (formed by the downwardly extending flap 8 and the upwardly extending dap 9 of the inner layer 2) is always open and accessible.

Figure 12:
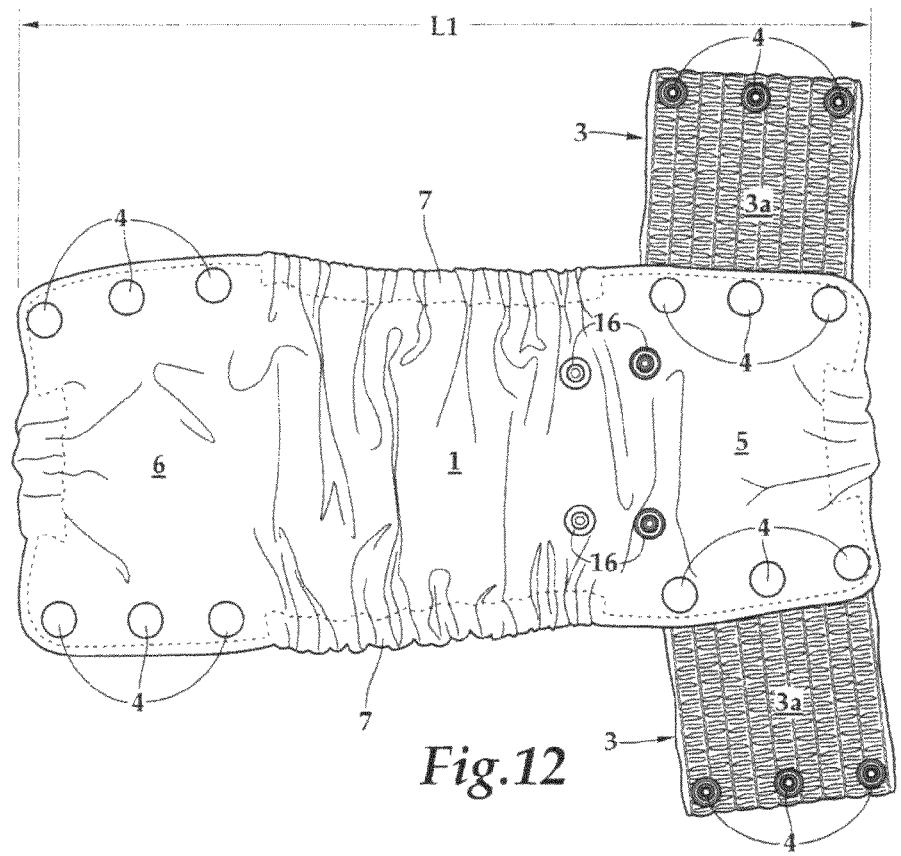
FIG. 12 is a plan view of the present invention shown with both side panels attached to the front portion of the diaper.
Figure 13:
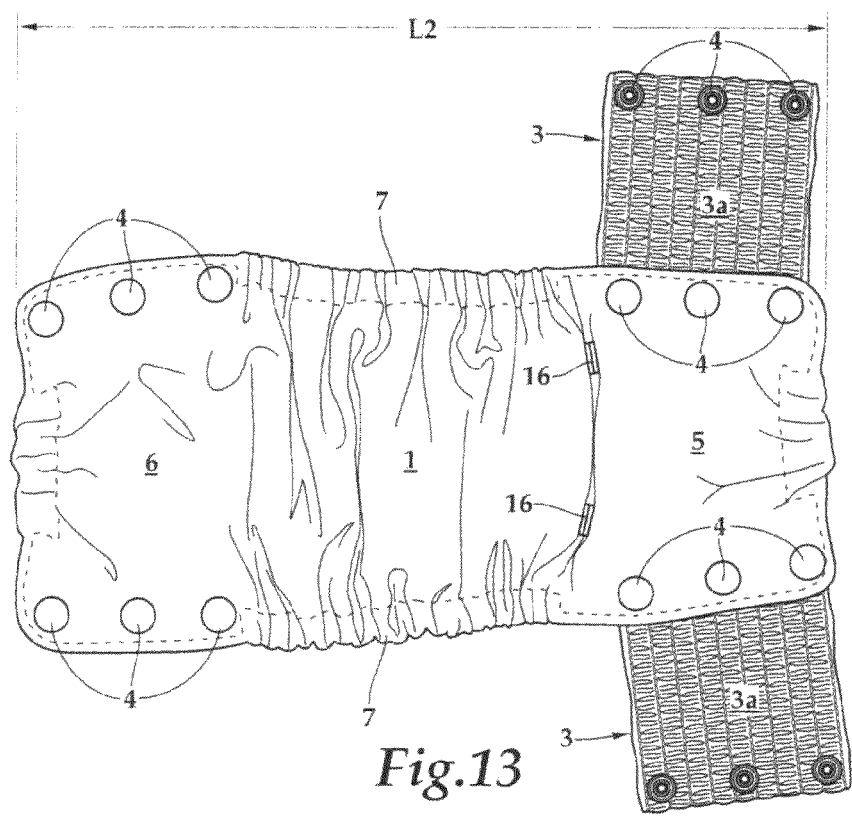
FIG. 13 is a plan view of the present invention shown with both side panels attached to the front portion of the diaper and the front portion folded back on itself and snapped in place to adjust the size of the diaper.

FIGS. 12 and 13 illustrate the function of the rise snaps 16 of the present invention. As shown in this figure, the size of the training diaper can be adjusted (shortened in front) by folding the front portion 5 of the outer layer 1 onto itself and snapping the two pairs of rise snaps 16 together.

In a preferred embodiment, the outer layer 1 and smocked material 3a are both comprised of a thermoplastic polyurethane material. In a preferred embodiment, the inner layer 2 is comprised of a polyester athletic wicking fabric, and the non-smocked material 3b of the side panel 3 is comprised of a knit polyester.

Although the preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

I claim:
1. A cloth training diaper comprising:
(a) an outer layer coupled to an inner layer;
(b) a front portion and a rear portion;
(c) a plurality of snaps arranged longitudinally along the right side of the front portion, the left side of the front portion, the right side of the rear portion, and the left side of the rear portion, the snaps extending through the outer and inner layers; and
(d) two side panels, each side panel comprised of a smocked material coupled to a nom-smocked material, each side panel having a right side and a left side and a plurality of snaps arranged along the right and left sides of the smocked material, wherein the snaps on the side panels engage with the snaps on the front and rear portions.

2. The cloth training diaper of claim 1, wherein the smocked material of the side panels is formed by weaving elastic thread through a layer of fabric.

3. The cloth training diaper of claim 1, further comprising a pocket that is disposed between the inner and outer layers and that extends longitudinally from a top of the front portion to a top of the rear portion and that is as wide as the front and rear portions.

4. The cloth training diaper of claim 3, wherein the front portion and the rear portion each comprises an elasticized top, wherein the inner layer is comprised of a first piece of material and a second piece of material, wherein the first piece of material forms a downwardly extending flap proximate the elasticized top of the rear portion, and wherein the second piece of material forms an upwardly extending flap that lies on top of the downwardly extending flap to form an opening for the pocket.

5. The cloth training diaper of claim 1, further comprising two pairs of rise snaps on the front portion on the outer layer.

\* \* \* \* \*